United States Patent [19]
Giliberty

[11] 3,982,281
[45] Sept. 28, 1976

[54] HIP-JOINT PROSTHESIS DEVICE
[76] Inventor: Richard P. Giliberty, 824 Hunt Lane, Manhasset, N.Y. 11030
[22] Filed: July 25, 1975
[21] Appl. No.: 598,752

[52] U.S. Cl. .............................. 3/1.913; 128/92 C; 128/92 CA
[51] Int. Cl.² .......................................... A61F 1/24
[58] Field of Search ........................... 3/1.9–1.913, 3/1; 128/92 C, 92 CA

[56] References Cited
UNITED STATES PATENTS
3,813,699  6/1974  Giliberty .............................. 3/1.912
3,903,549  9/1975  Deyerle ................................ 3/1.912

Primary Examiner—Ronald L. Frinks
Attorney, Agent, or Firm—Bauer, Amer & King

[57] ABSTRACT

The patented prosthesis device of U.S. Pat. No. 3,813,699 is effectively limited in its drifting movement deeper into its cooperating acetabular opening, which could cause rupture of the acetabular floor, by a laterally oriented lip, even though the size of the lip, in and of itself, is not physically capable of this performance. This is achieved by providing an initial clearance position to the lip and thus allowing a settling movement in the device before the lip is permitted to contact bone structure. During said settling movement, favorable secondary tissue changes occur in the acetabular opening which impede movement; thus, said tissue changes together with the lip making contact with bone structure hold the device in position, whereas premature contact of the lip would have merely indented or otherwise adversely modified the bone structure and interfered with achieving this result.

5 Claims, 5 Drawing Figures

U.S. Patent  Sept. 28, 1976  3,982,281
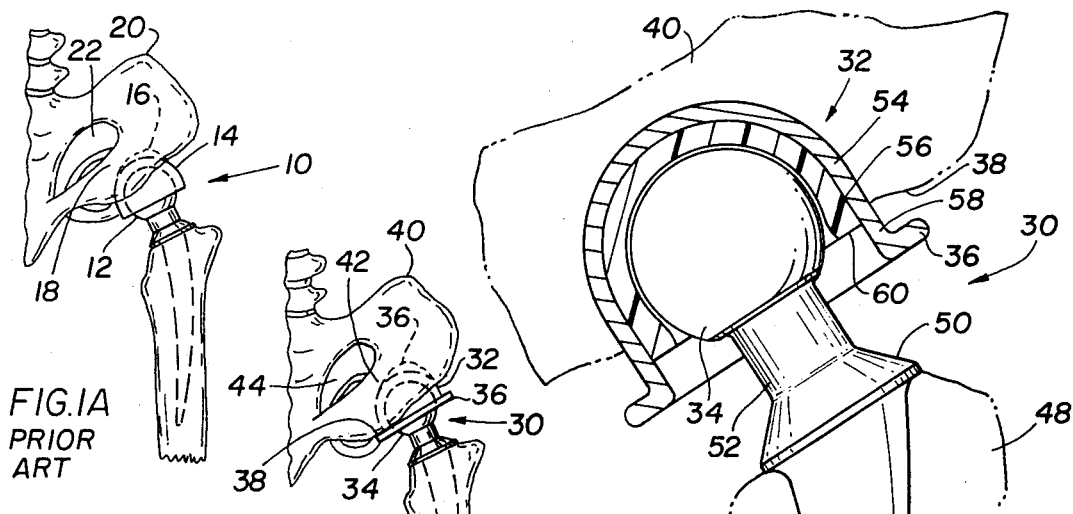
FIG.1A PRIOR ART
FIG.1B PRIOR ART
FIG.3
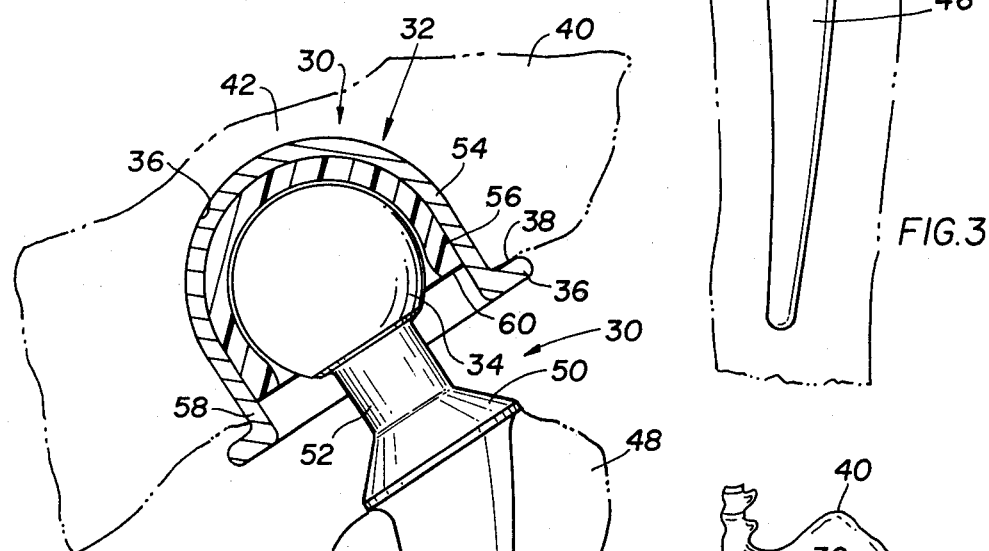
FIG.4
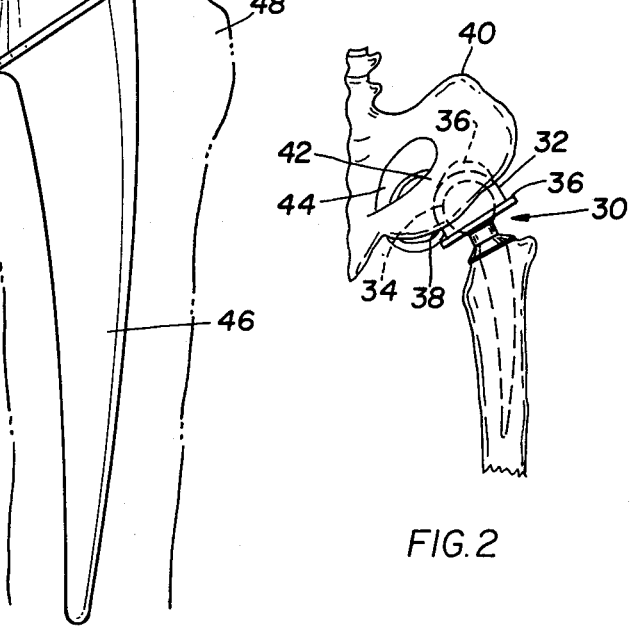
FIG.2

HIP-JOINT PROSTHESIS DEVICE

The present invention relates generally to a hip-joint prosthesis device, of the type surgically implanted in a shaped and sized acetabular opening, and as described and illustrated in U.S. Pat. No. 3,813,699, and more particularly, to an improved version of said type device which, due to its improvements, achieves a stabilized position within the cooperating acetabular opening which minimizes rupture of the acetabular floor and the condition of acetabula protrusio.

The forerunner patented prosthesis device is, according to medical practice, surgically implanted in a cooperating acetabulum opening, the deformity of which is removed by reaming said opening down to the shape and size of a normal acetabulum opening. The removal of tissue and bone, however, significantly increases the possibility of the device, during use, projecting through the acetabulum floor into the pelvis, and thus giving rise to the adverse condition of acetabula protrusio.

Providing movement-limiting structure, such as a lip, on the outer surface of the device has not proven effective, because the nominal additional surface added in the form of the lip in contact with bone structure, has not been able to prevent penetration of the lip into the bone structure under the concentrated stresses and forces of normal use, to say nothing of the forces that develop from a blow or fall. In fact, the indentation into the contacted bone structure by the lip aggravates the situation in that it detracts from effective functioning of the device.

Broadly, it is an object to provide a movement-limiting lip structure to the device which is so applied as to achieve position stability thereof, and which nevertheless does not have the foregoing and other shortcomings of the prior art. Specifically, it is an object to provide a position-stabilizing lip in a selected position on the device so as to resist movement only after a tissue-forming interval, and thus when said formed tissue can and does assist the lip in preventing further drifting movement of the device.

An improved hip-joint prosthesis device of the present invention includes the patented structural features of an assembly of outer and inner spherical cups frictionally engaged about a spherical head of the device and has, as a significant improvement to its outer spherical cup, a cylindrical wall section thereon which extends in pending relation beyond its inner cup so as to define a clearance space for an initial settling movement of the device within its cooperating acetabular opening. That is, on said cylindrical wall is a laterally oriented lip adapted to engage the anatomical bounding structure of the acetabular opening only after said settling movement. This delayed or postponed contact permits favorable secondary tissue changes to first occur in the acetabular opening to assist the lip in holding the device in position when said contact ultimately occurs.

The above brief description, as well as further objects, features and advantages of the present invention, will be more fully appreciated by reference to the following detailed description of a presently preferred, but nonetheless illustrative embodiment in accordance with the present invention, when taken in conjunction with the accompanying drawings, wherein:

FIGS. 1A and 1B are side elevational views of prior art hip-joint prosthesis devices which illustrate the environment of the invention and additionally contribute to an understanding of the improvement represented by the hip-joint prosthesis device of the present invention.

The remaining figures illustrate the improved hip-joint prosthesis device hereof, FIG. 2 more particularly being a side elevational view, in reduced scale, illustrating the initial position of the prosthesis device in the patient's acetabular opening;

FIG. 3 being a side elevational view like FIG. 2, but in enlarged scale, to thereby better illustrate the structural features and functional aspects of the device hereof; and FIG. 4 is a side elevational view of the same, in the enlarged scale of FIG. 3, but illustrating the device after settling movement of the prosthesis device within its cooperating acetabular opening.

Reference is now made to the drawings and in particular to FIGS. 1A and 1B which illustrate the environment for the improved prosthesis device hereof, and also prior art efforts at providing effective and efficiently functioning embodiments thereof. Specifically, intended to be illustrated in FIG. 1A is a surgically implanted hip-joint prosthesis device, generally designated 10, which is of the type illustrated and described in detail in U.S. Pat. No. 3,813,699. Device 10 includes a spherical head 12 which is force-fit in an assembly 14 of outer and inner cups. Assembly 14, in turn, is surgically implanted in an acetabulum opening 16 which is reamed to an appropriate shape and dimension necessary to accommodate the prosthesis device 10 with its cup assembly 14. That is, in accordance with medical practice, the deformed acetabulum opening is reamed down to cancellous bone in the shape and dimension of a relatively normal acetabulum opening incident to the implantation therein of the prosthesis device 10. It has been found in practice, however, that placement of the acetabulum opening into the proper shape and size for the prosthesis device 10 seriously reduces the acetabulum floor 18 of the hip 20 which, after an interval of use, then results in a drift of the prosthesis device 10 through the floor 18 into the pelvis 22.

To prevent the foregoing, or what is known as acetabula protrusio, use has been made of the modified prosthesis device 30 illustrated in FIG. 1B. Device 30, like device 10, has an assembly of outer and inner cups force-fit on a spherical head 34, and the same is surgically implanted in a properly shaped and dimensioned acetabulum opening 36. However, in an effort to prevent drift of the prosthesis device 30 into the pelvis, the outer cup of the assembly 32 has a laterally oriented lip 36, some portion of which engages, as at 38, the bone structure of the hip 40 which bounds the acetabulum opening 36. The purpose is of course to limit the inwardly drifting movement of the assembly 32 so that there is no penetration through the acetabulum floor 42 into the pelvis 44. Unfortunately, even the additional surface area contributed by the lip 36, as well as its orientation normal to the direction of the drifting movement when mechanically fixed by screws and/or cement to the acetabular rim, has not proven in practice to be effective in preventing acetabula protrusio, although there is some improvement over the prosthesis embodiment 10 of FIG. 1A. It is believed that the inability of the lip 36 to prevent drifting movement is due to the elasticity of the living bone which differs so significantly from metal as to be ineffective to prevent, under the forces involved, the penetration of the lip-contacting surface 38 into the bone which it contacts. Device 30, by avoiding rigid fixation with the rim of the acetabulum, circumvents this incompatibility and the impact forces will dissipate because of the relative movement between the limiting lip structure and the tissue formed between this interface and the bony rim of the acetabulum. With prior art the rigid fixation disrupts with cyclic loading of the hip joint and causes a failure of the device.

Reference is now made to FIG. 2 illustrating the improved prosthesis device of the present invention, the improvements perhaps being more readily understood and recognized by comparison of FIG. 2 with FIG. 1B. To facilitate this recognition and understanding, similar structural features of the improved prosthesis device hereof and of the device of FIG. 1B are designated by the same reference numerals used for the prosthesis device of FIG. 1B. As will be explained in greater detail subsequently, the significant difference embodied in the device 30 of FIG. 2 is that upon initial implantation of the device in the manually shaped and sized acetabulum opening 36, the laterally oriented lip 36 of the outer cup of assembly 32 is out of contact with, i.e. occupies a clearance position from, the acetabulum bone structure 38 which bounds the opening. However, lip 36 is obviously a part of the construction, whereas it was not in the FIG. 1A embodiment, and thus after an initial drift, or what may be more accurately referred to as a settling movement of the prosthesis device 30, it will of course be recognized that lip 36 will make contact with the bone structure 38. It has been found in practice that the subsequent contact made after a settling movement of the prosthesis device of the laterally oriented lip 36 with the hip 40 is effective in limiting further drifting movement of the prosthesis into the hip and thus effectively prevents and minimizes acetabula protrusio. In this connection, underlying the present invention is the recognition that immediately after the surgical implantation of a prosthesis device, such as device 30, that secondary tissue changes occur in the reshaped and sized acetabulum opening. Specifically, on the surface 38 bounding the opening there may be a forming of fibro cartilage and hyaline cartilage with synovia lining, all of which may be conveniently referred to as cartilaginous metaplasia. Stated still another way, after the initial surgical implantation of the prosthesis device 30, a fibro cartilage lining will develop in the reshaped and dimensioned acetabulum opening which is compatible in appearance and function to a normal acetabulum.

As a consequence of the foregoing, it has been recognized that although what is intended to be a movement-limiting structural feature, such as the lip 36, is not effective in and of itself to achieve its end result or objective, nevertheless this objective can be achieved with the assistance of the secondary tissue changes which occur after the surgical implantation of the prosthesis device. Thus, where the lip 36 occupies a position adjacent living bone structure 38 at the time of implantation, and thus before the availability of the secondary tissue changes, there will be drifting movement of the prosthesis device into the hip 40 despite the lip 36. Even more important, drifting movement at this time aggravates the situation since the laterally extending lip 36, as well as the assembly 32, creates an indentation into the hip 40. On the other hand, in the situation depicted in FIG. 2, simultaneously with slight drifting movement of the prosthesis device 30 into the hip 40 there is, as already indicated, the formation of secondary tissue changes which has the capacity to impede the drifting movement, and said secondary tissue changes together with the lip 36, when it finally comes in contact 38 with the hip 40, results in effectively preventing any further drifting movement of the prosthesis device 30 as might result in rupture of the acetabular floor 42 and in a secondary acetabular protrusion.

Reference is now made to FIGS. 3 and 4 which illustrate, on an enlarged scale, the improved hip-joint prosthesis device 30 of FIG. 2 and additionally, the initial, or surgical implantation position, of the device 30 and its subsequent position after settling movement thereof. For completeness sake, it will be understood that device 30 includes a stem 46 that is adapted to be forced into the femur 48 after the natural head has been removed. Appropriately machined on the stem 46 is a conical stop of positioning shoulder 50, a reduced diameter neck 52, and finally the previously referred to spherical head 34.

The previously referred to assembly 32 consists of an outer cup member or liner 54, preferably constructed of metal, such as Zimaloy, Vitallium, or stainless steel. The inner cup 56 is preferably composed of a material having a low frictional resistance and a high lubricating characteristic, and may include such materials as silicone, polyethylene, and polyfluroethylene. The structural features and construction materials of the prosthesis device just generally described are similar to the prosthesis device patented by one of the joint inventors hereof in U.S. Pat. No. 3,813,699. The improvement to said prosthesis device, which as already indicated significantly minimizes the occurrence of acetabula protrusio is applied to the outer cup member 54. Specifically, cup 54 is modified to differ from its patented counterpart so as to include a cylindrical wall section 58 extending in pending relation beyond the lower edge 60 of the inner cup 56. Thus, wall section 58, as best illustrated in FIG. 3, is effective in providing a clearance position to the laterally oriented previously noted lip 36 in relation to the bone structure 38 of hip 40. From its starting surgically implanted position illustrated in FIG. 3, the prosthesis device 30 hereof undergoes settling movement which results in its drifting inwardly of hip 40 and thus into the acetabular floor 42 thereof, as illustrated in FIG. 4. As further illustrated in FIG. 4, following settling movement of the device 30, ultimately contact, as at 38, is established between at least a portion of the lip 36 and the hip 40. Since during said settling movement of the device 30 secondary tissue changes have occurred in the wall bounding the acetabulum opening 36, for the reasons already discussed in connection with FIG. 2, lip 36 with the assistance of these secondary tissue changes is effective in preventing any further drifting movement in the prosthesis device 30. As a consequence, the occurrence of acetabula protrusio, or rupturing of the acetabular floor 42 is significantly minimized, thereby greatly adding to the beneficial use of the hip-joint prosthesis device 30.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. In a hip-joint prosthesis device of the type surgically implanted in a manually shaped acetabular opening having an assembly of outer and inner spherical cups frictionally engaged about a spherical head of said device, the improvement to said outer spherical cup comprising a cylindrical wall section thereon extending in pending relation beyond said inner cup so as to define a clearance space for settling movement of said device within said acetabular opening, and a laterally oriented lip on said wall section adapted to engage the anatomical bounding structure of said acetabular opening only after said settling movement of said device, whereby said lip is assisted in limiting the settling movement of said device by favorable secondary tissue changes occurring in said acetabular opening prior to said engaging contact of said lip.

2. An improved hip-joint prosthesis device as claimed in claim 1 wherein said inner cup extends in covering relation about said spherical head to an extent sufficient to obviate frictional disengagement therebetween, and said depending outer cup cylindrical wall section extends beyond said inner cup so as to locate said lip thereon in a clearance position from said acetabular opening anatomical bounding structure, whereby said device during said settling movement is not restricted by said lip from partaking of pivotal movement in said acetabular opening.

3. An improved hip-joint prosthesis device as claimed in claim 2 wherein said outer cup depending wall section bounds an internal clearance adjacent the termination of said inner cup, whereby said inner cup is not restricted from movement into said clearance relative to said outer cup.

4. An improved hip-joint prosthesis device as claimed in claim 3 wherein said outer cup depending cylindrical wall section and laterally oriented lip thereon define an L-shape in cross-section, whereby one leg thereof functions effectively to limit movement in the direction of said other leg upon contact with a stationary object in said direction of movement.

5. An improved hip-joint prosthesis device as claimed in claim 4 wherein said L-shape is located below said spherical head of said prosthesis device and contributes to the structural rigidity bounding said opening into said outer cup to in turn assist in maintaining said cups in their engaged relation about said spherical head.

* * * * *